United States Patent
Grady et al.

(10) Patent No.: US 10,112,759 B2
(45) Date of Patent: Oct. 30, 2018

(54) SINGLE DOSE MATERIAL AND APPLICATOR PACKAGE

(71) Applicant: Centrix, Inc., Shelton, CT (US)

(72) Inventors: Jay Grady, Wolcott, CT (US); Robert Nordquist, Wilton, CT (US)

(73) Assignee: Centrix, Inc., Shelton, CT (US)

( * ) Notice: Subject to any disclaimer, the term of this patent is extended or adjusted under 35 U.S.C. 154(b) by 0 days.

(21) Appl. No.: 15/436,977

(22) Filed: Feb. 20, 2017

(65) Prior Publication Data

US 2018/0237198 A1    Aug. 23, 2018

(51) Int. Cl.
*B65D 75/36* (2006.01)
*B65D 75/54* (2006.01)
*A61C 19/00* (2006.01)

(52) U.S. Cl.
CPC .......... *B65D 75/367* (2013.01); *A61C 19/005* (2013.01); *B65D 75/54* (2013.01)

(58) Field of Classification Search
CPC ......... A61B 50/30; A61B 50/33; A61C 19/00; A61C 19/005; A61C 3/00; A61C 3/005; A61L 9/00; B65D 75/367; B65D 75/42; B65D 75/54; B65D 69/00; B65D 75/167; B65D 75/36; B65D 75/58; B65D 75/5835; B65D 81/32; B65D 81/3255; A61M 35/00; A61M 35/003
USPC ........................................ 206/63.3, 363–369
See application file for complete search history.

(56) References Cited

U.S. PATENT DOCUMENTS

| | | | | |
|---|---|---|---|---|
| 4,019,633 | A * | 4/1977 | Roth | A61F 6/14 206/364 |
| 5,542,533 | A * | 8/1996 | Vargas, III | A61B 50/33 206/363 |
| 5,660,273 | A | 8/1997 | Discko, Jr. | 206/229 |
| 5,954,996 | A | 9/1999 | Discko, Jr. | 252/79.1 |
| D421,217 | S | 2/2000 | Discko, Jr. | D6/415 |
| 6,116,414 | A | 9/2000 | Discko, Jr. | 206/229 |
| 6,228,324 | B1 * | 5/2001 | Hasegawa | A61L 2/208 206/364 |
| 6,328,159 | B1 | 12/2001 | Discko, Jr. | 206/229 |
| 6,405,735 | B1 * | 6/2002 | Dockery | A45D 29/007 206/363 |
| 6,685,013 | B2 | 2/2004 | Discko, Jr. | 206/229 |
| 6,959,808 | B2 | 11/2005 | Discko, Jr. | 206/229 |
| 7,243,789 | B2 | 7/2007 | Discko, Jr. | 206/229 |
| 7,828,142 | B2 | 11/2010 | Discko, Jr. | 206/229 |
| 8,656,929 | B2 * | 2/2014 | Miller | A61B 50/30 128/898 |

(Continued)

*Primary Examiner* — Bryon Gehman
(74) *Attorney, Agent, or Firm* — Fattibene and Fattibene LLC; Paul A. Fattibene

(57) ABSTRACT

A single dose material and applicator package that is easily held for removal of a cover and that contains an easily removable applicator. A tray has an applicator well and a material well. Formed in the applicator well is a finger depression adjacent the material well and an applicator support depression adjacent an opposing end of the applicator well. The finger depression permits easy grasping of the tray for removing the cover. The applicator support depression acts as a fulcrum to pivot or lever the applicator out of the tray when a force is applied to one end of the applicator. A material well ramp permits a controlled amount of material to be placed on the applicator brush.

3 Claims, 6 Drawing Sheets

(56) References Cited

U.S. PATENT DOCUMENTS 9,808,570 B2 * 11/2017 Head .................... A61M 5/002
2003/0146116 A1   8/2003 Klein et al. .................. 206/229

* cited by examiner

SINGLE DOSE MATERIAL AND APPLICATOR PACKAGE

FIELD OF THE INVENTION

The present invention relates in general to a package for holding a material and applicator, and more particularly to a single dose package making applying a material to a surface easy, precise, and convenient

BACKGROUND OF THE INVENTION

In many applications and in particular medical procedures a relatively small quantity of material must be accurately and precisely placed to a surface being treated. It is often necessary that the material and applicator be maintained in a sterile or uncontaminated condition. It is convenient that only a single dose of material be provided so as to prevent cross contamination between patients during a medical procedure.

There are a large number of packaging systems for holding a material and applicator. One such packaging system is disclosed in U.S. Pat. No. 5,660,273 entitled "Single Patient Dose Medicament Dispenser with Applicator" issuing to John J. Discko, Jr. on Aug. 26, 1997, which is herein incorporated by reference. Therein disclosed is a tray having wells for holding the material and a portion of an applicator. The applicator extends out of the rear of the tray. A removable cover is placed on a top surface of the tray covering the material well and a portion of the applicator. While this package has many advantages the sterility and cleanliness of the applicator cannot be assured due to a portion of the applicator extending from the tray that is not covered. Additionally the tray is often difficult to hold while removing the cover from the material well. Also, the quantity of material placed on the applicator could not be precisely controlled potentially resulting in more material being applied than desired.

In packages that contain the entire applicator, is often difficult to remove the applicator from the package. Removal of the applicator is often complicated or difficult when gloves are used, such as in a medical procedure. This often results in the applicator not being securely held increasing the potential of dropping the applicator resulting in contamination making the applicator unsuitable for a medical procedure.

Accordingly, there is a need for a package that can hold a material and applicator that assures sterility or cleanliness to both the material and applicator and that is easy to hold so that the cover can be more easily be removed. There is also a need for a package containing an applicator and a material in which the quantity of the material placed on the applicator and delivered to a surface can be controlled.

SUMMARY OF THE INVENTION

The present invention is a single dose material and applicator package that makes dispensing a material convenient and easy. A formed tray has a material well and an applicator well formed therein. Also formed in the tray is a finger depression and applicator support. The material well has a ramp formed therein. A removable cover covers a top surface of the tray securely sealing the material and applicator therein.

In one embodiment additional depressions are formed in the tray so as to hold and center the applicator within the applicator well.

It is an object of the present invention to provide a package making dispensing a material easy and convenient.

It is another object of the present invention to provide a package assuring that the material and applicator may be maintained in a sterile condition or free from contamination.

It is an advantage of the present invention that it is easily held and provides a secure grip for removing the cover.

It is another advantage of the present invention that the applicator is easily removed, even with gloved hands.

It is another advantage of the present invention that the amount or quantity of material contained on the applicator can be conveniently regulated or controlled.

It is a feature of the present invention that a finger depression is formed in the tray providing a secure grip on the package.

It is another feature of the present invention that an applicator support creates a fulcrum adjacent an end of the applicator well permitting the applicator to be easily pivoted or levered upward for easy removal from the tray.

It is another feature of the present invention that a ramp is formed in the material well permitting the quantity of material contained on the applicator to be regulated or controlled.

These and other objects, advantages, and features will become more readily apparent in view the following more detailed description.

DETAILED DESCRIPTION OF THE PREFERRED EMBODIMENT

FIGS. 1-10 illustrate a first embodiment of the single dose material and applicator package 10 of the present invention.

Figure 1:
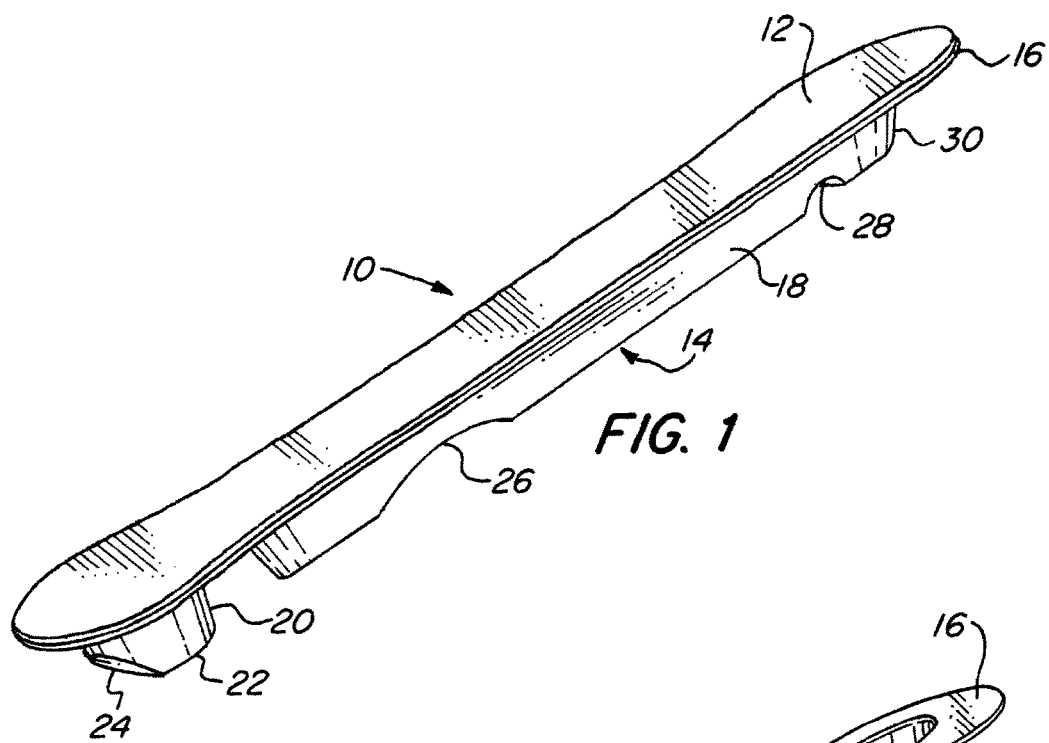
FIG. 1 is a perspective view of a first embodiment of the present invention with the cover attached.
Figure 2:
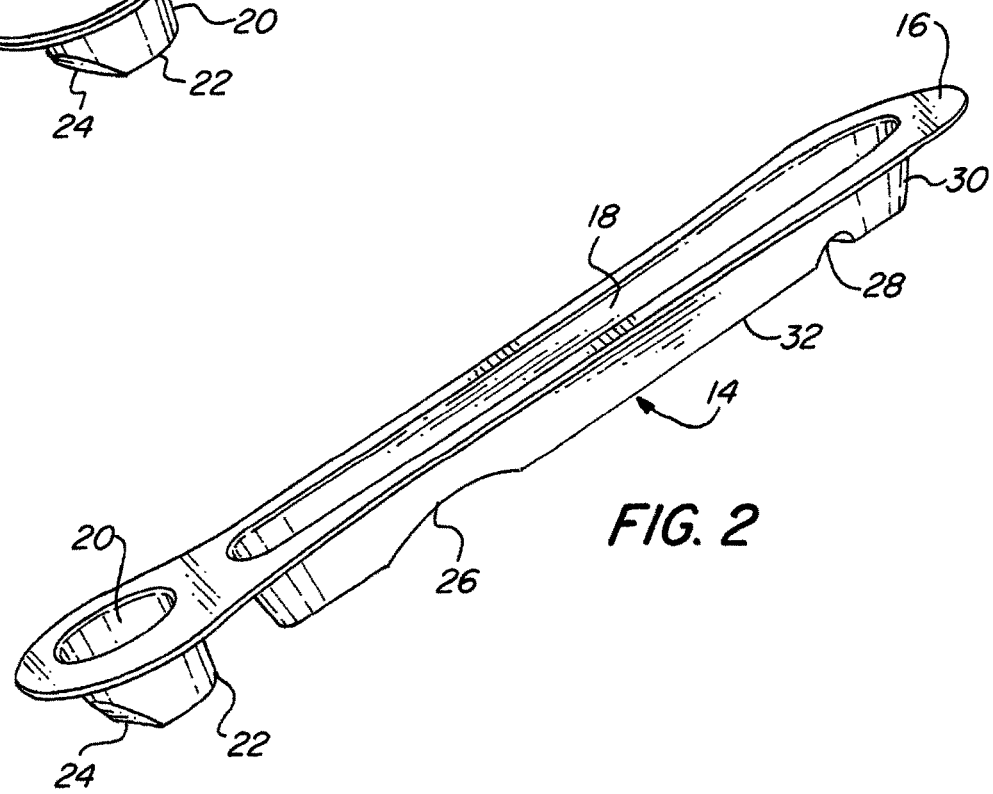
FIG. 2 is a perspective view of the first embodiment of the present invention with the cover removed.
Figure 3:
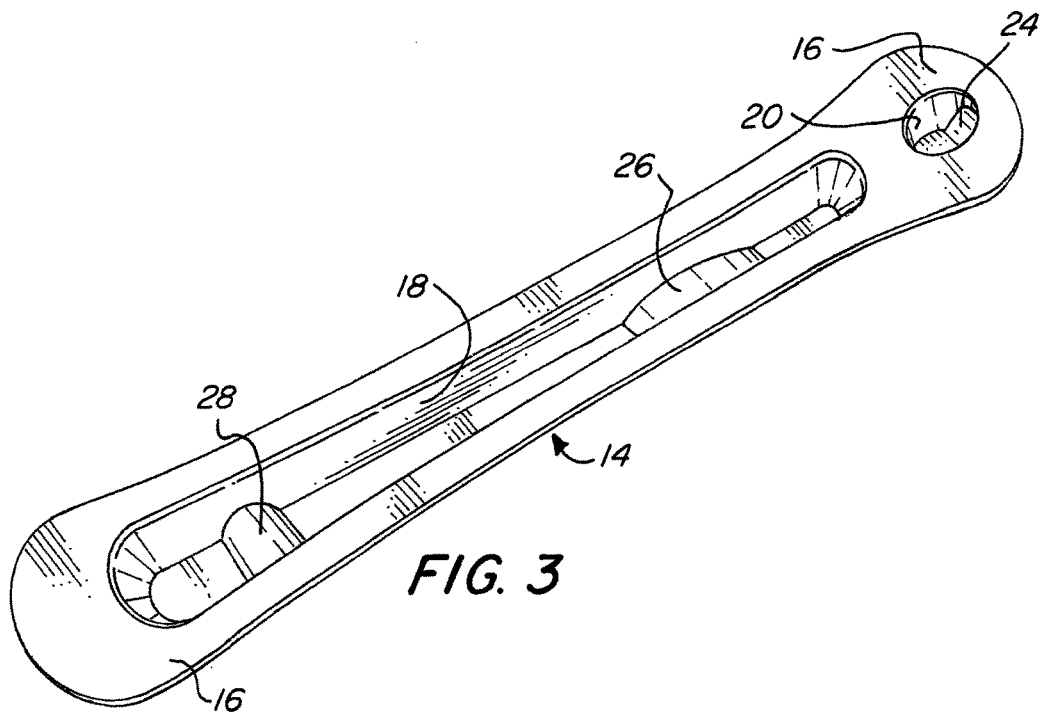
FIG. 3 is a perspective view of the first embodiment of the present invention with the cover removed at a different angle.
Figure 4:
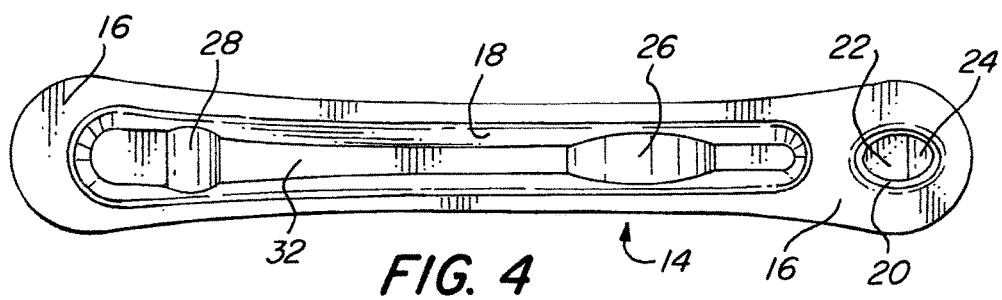
FIG. 4 is a top plan view of the first embodiment of the present invention without the cover.
Figure 5:
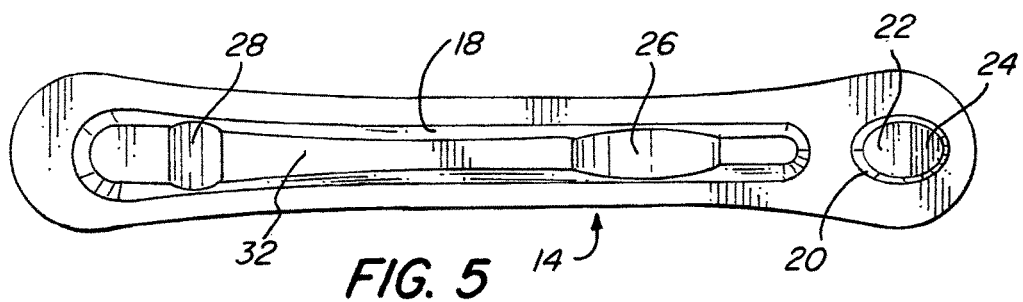
FIG. 5 is a bottom plan view of the first embodiment of the present invention.
Figure 6:
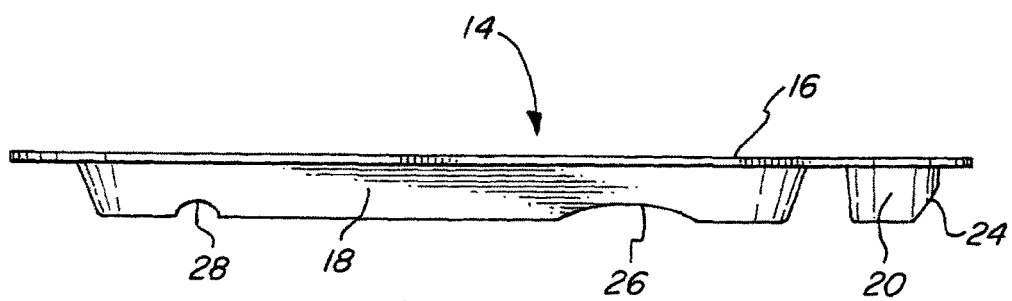
FIG. 6 is a side elevational view of the first embodiment of the present invention.
Figure 7:
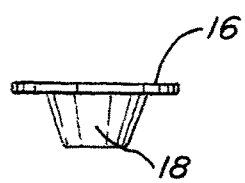
FIG. 7 is a rear elevational view of the first embodiment of the present invention.
Figure 8:
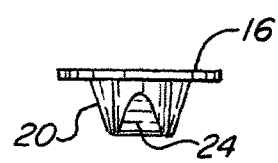
FIG. 8 is a front elevational view of the first embodiment of the present invention.

FIG. 1 is a perspective view illustrating a formed tray 14 with the removal cover 12. The removable cover 12 is removably attached to a surface of the tray 14. The formed tray 14 may be made of any suitable plastic material and preferably vacuum molded, but also may be injection molded. A portion of the cover 12 or a tab may overhang an edge of the tray facilitating removal of the cover. Alternatively, a small portion of the cover 12 may not be attached to the tray 14 facilitating removal. The cover preferably is made of a durable impermeable material, such as a plastic laminated foil. The cover may be adhesively fixed, heat sealed, ultrasonically welded, to the tray 14 or affixed by other equivalent sealing means.

FIGS. 2-10 additionally illustrate the first embodiment of the present invention with the cover removed providing a better view of the features of the present invention. Formed within the tray 14 are several depressions that greatly facilitate the use and function of the single dose material and applicator package 10. Formed within the tray 14 are a flange 16, an applicator well 18, and a material well 20. The flange 16 forms a planar surface above the applicator well 18 and the material well 20. Formed within the material well 20 are a material well bottom 22 and a material well ramp 24. The material well ramp 24 forms an angular surface between the flange 16 and the material well bottom 22. Also formed within the tray 14 in the bottom 32 of the applicator well 18 is a finger depression 26 and a first applicator support depression 28. The applicator support depression 28 is adjacent a rear end 30 of the tray 14. The finger depression 26 forms a first applicator support protrusion on the inside of the applicator well 18. The applicator support depression 28 forms a second applicator support protrusion on the inside of the applicator well 18.

The finger depression 26 and the applicator support depression 28 extend into the applicator well 18. An applicator 34, illustrated in FIGS. 9-10 rests on the surface of the finger depression 16 and the surface of the applicator support depression 28 on the inside of the applicator well 18.

Figure 9:
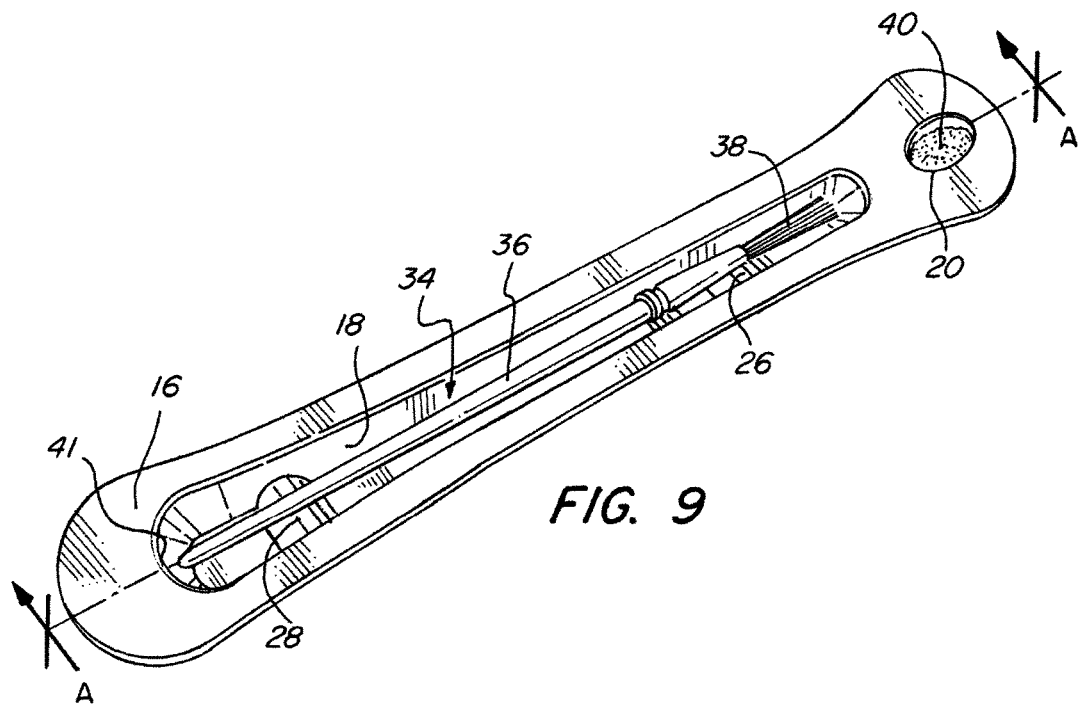
FIG. 9 is a perspective view of the first embodiment of the present invention with an applicator and material placed therein.
Figure 10:
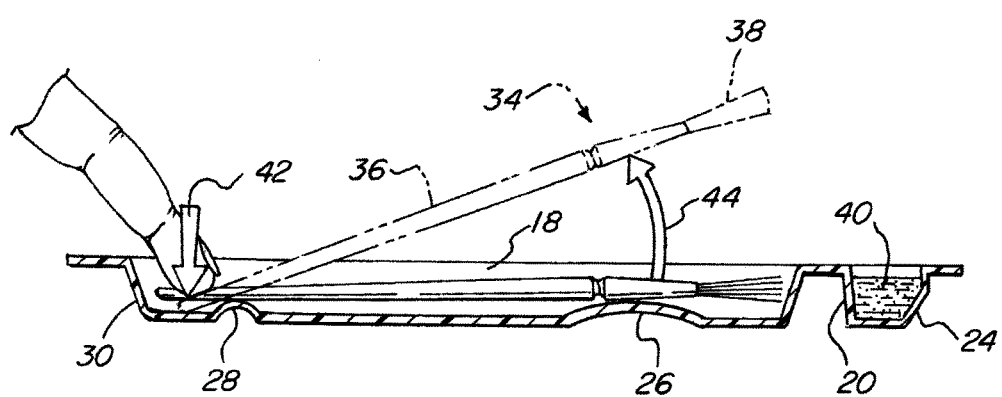
FIG. 10 is a partial cross section taken along line A-A in FIG. 9 illustrating the removal of the applicator.
Figure 11:
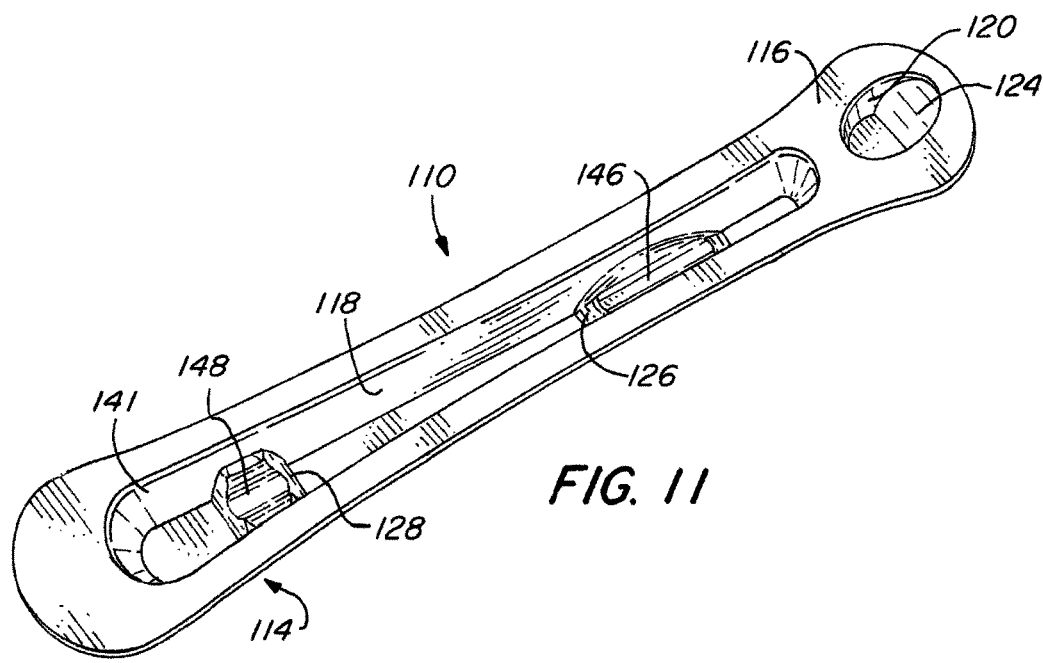
FIG. 11 is a perspective view of a second embodiment of the present invention with the cover removed illustrating additional depressions for centering the applicator.
Figure 12:
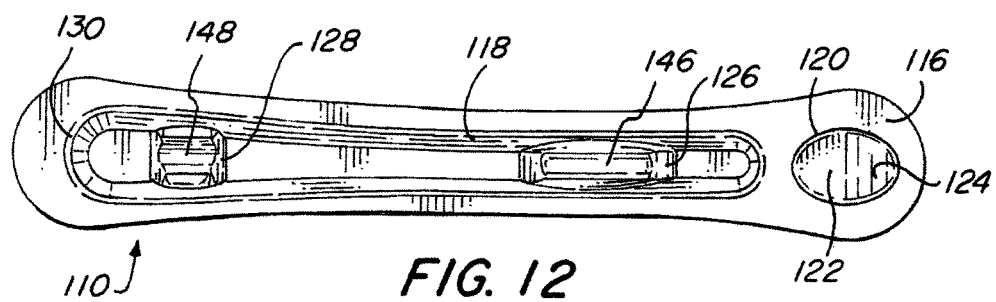
FIG. 12 is a top plan view of the second embodiment of the present invention.
Figure 13:
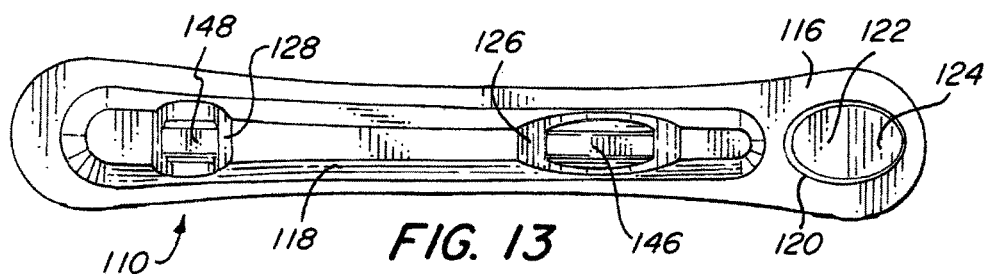
FIG. 13 is a bottom plan view of the second embodiment of the present invention.
Figure 14:
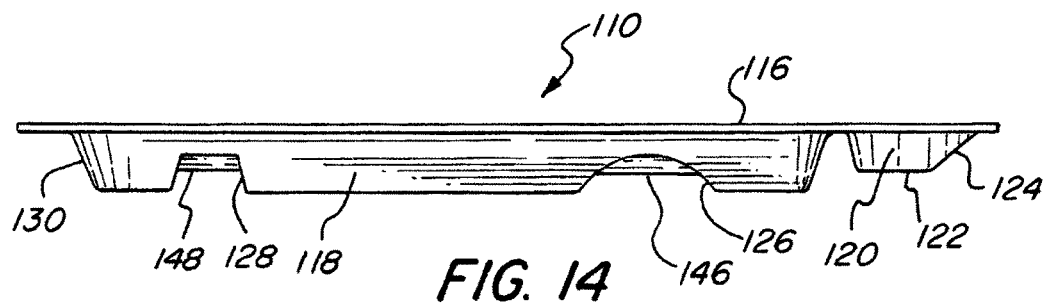
FIG. 14 is a side elevational view of the second embodiment of the present invention.
Figure 15:
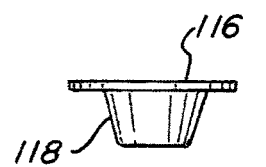
FIG. 15 is a rear elevational view of the second embodiment of the present invention.
Figure 16:
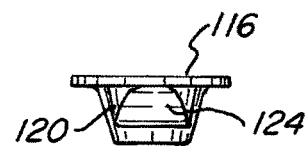
FIG. 16 is a front elevational view of the second embodiment of the present invention.

The applicator 34, illustrated in FIGS. 9 and 10, has an applicator handle 36 and an applicator brush 38. The applicator brush 38 may be any type of applicator brush that can hold the material, such as bristles, foam material, or flocking. The finger depression 26 supports a portion of the applicator 34 adjacent the applicator brush 38 and the applicator support depression 28 supports a portion of the applicator 34 adjacent a distal end of the handle 36. A material 40 is placed within the material well 20. The material 40 may be any type of material such as a paste, gel or liquid. Preferably the material 40 is a medicinal material and preferably a dental material. The dental material may be any material used in dentistry such as a cement, sealant, disinfectant, desensitizers, fluoride material, or any other material to be coated on a surface.

One of the advantages of the present invention is illustrated in FIG. 10. As illustrated in FIG. 10, the applicator 34 is easily removed from the applicator well 18 by pressing on the distal end of the applicator handle 36 with a finger. Arrow 42 presents downward pressure applied by a user's finger on the distal end of the applicator handle 36. A wider portion 41, illustrated in FIG. 9, adjacent the rear end 30 of the applicator well 14 has an increased lateral dimension relative to the lateral dimension of a major longitudinal length of the applicator well 18. The wider portion 41 provides sufficient width or lateral dimension for insertion of a user's finger. The lateral dimension of the wider portion 41 should be sufficiently large to accommodate the width of a user's finger. As the user presses on the distal end of the applicator handle 36 of applicator 34 the applicator handle 36 pivots on the applicator support depression 28 acting like a fulcrum to lever upward the applicator handle 36 and the applicator brush 38 so that the applicator 34 may be easily grasped by the user. Therefore, the applicator 34 is easily removed from the applicator well 18 even when the width of the applicator 34 matches closely to the width of the applicator well 18. This reduces the amount of material used in the tray 14 and more securely holds the applicator 34 within the applicator well 18, and yet permits easy removal of the applicator 34 from the applicator well 18.

Once the applicator 34 is removed from the applicator well 18 and tray 14, the applicator brush 38 may be dipped within the material 40 and applied to a surface. To control the amount of material on the applicator brush 38 to be applied to a surface, the applicator brush 38 may be rubbed on the material well ramp 24 so as to remove a desired amount of material 40 therefrom. This provides a means for controlling the amount of material 40 applied to a surface by the applicator brush 38.

FIGS. 11-16 illustrate a second embodiment of a single dose material and applicator package 110 of the present invention. In this embodiment a front applicator channel 146 and a rear applicator channel 148 aid in centering and holding an applicator in the applicator well 118. The handle of an applicator, not shown, is held by the front and rear applicator channels 146 and 148.

In FIGS. 11-16, a removable cover is not illustrated. However it should be appreciated that a removable cover similar to that illustrated in FIG. 1 is placed on the flange 116 in this second embodiment of a single dose material and applicator package 110.

As illustrated in FIGS. 11-16 the single dose material and applicator package 110 comprises a formed tray 114 having a flange 116. Also formed in the tray 114 are an applicator well 118 and a material well 120. The material well 120 has a material well ramp 124 formed therein. The applicator well 118 has a finger depression 126 and an applicator support depression 128 formed in the bottom thereof. The applicator well 118 has a rear end 130 formed therein. Between the rear end 130 and the applicator support depression 128 there is a wider portion 141 having a lateral dimension sufficient for the insertion of a finger of a user.

Formed in the finger depression 126 is a front applicator channel 146 and formed in the applicator support depression is a rear applicator channel 148. The front and rear applicator channels 146 and 148 aid in holding and centering and applicator when the applicator is placed within the applicator well 118. The front and rear applicator channels may extend slightly more than one-hundred and eighty degrees around a handle of an applicator so as to hold securely the applicator within the applicator well 118.

Additionally in this second embodiment, illustrated in FIGS. 11-16, the material well ramp 124 extends from the material well bottom 122 to the flange 116. In this second embodiment the material well ramp 124 can be used as a means to control the amount of material on an applicator brush irrespective of the amount of material placed in the material well 120, as a portion of the material well ramp 124 will extend out of the material. The material well ramp 124 may be textured or ribbed to aid in removing a controlled amount of material from an applicator brush.

The present invention provides an improved single dose material and applicator package that can be more firmly and easily held so the removable cover may be more easily removed. Additionally the applicator support depression acts like a fulcrum so that the applicator may be raised above the flange of the tray for easy removal by only placing a finger adjacent the rear end of the tray.

While the present invention has been described with respect to several different embodiments, it will be obvious that various modifications may be made without departing from the spirit and scope of this invention.

What is claimed is:

1. A single dose material and applicator package for dispensing a material comprising:
   a tray;
   an applicator well having a first end and a second end and a bottom formed in said tray;
   a material well formed in said tray adjacent the first end, said material well having a flat bottom and an opposing open end;
   a ramp formed in said material well angularly extending from the flat bottom towards the open end of said material well;
   a finger depression formed in the bottom of said applicator well adjacent said material well and extending into said applicator well;
   an applicator support depression formed in the bottom of said applicator well adjacent the second end of said applicator well and extending into said applicator well;
   an applicator comprising an applicator brush having a handle end, the applicator handle having a distal end, said applicator having an applicator width and placed within the applicator well and positioned on top of said finger depression and said applicator support depression;
   a wider portion of said applicator well formed adjacent the second end of said applicator well, said wider portion having a lateral dimension greater than a lateral dimension of a majority of said applicator well that matches the applicator width, wherein the applicator brush end is placed adjacent the material well and the distal end of the applicator handle is placed within said wider portion of said applicator well, and the lateral dimension of said wider portion is sufficiently large to accommodate a width of a user's finger;
   a material placed within said material well;
   a flange formed in a top surface of said tray; and
   a cover removably affixed to said flange,
   wherein when said cover is removed a user is capable of pressing on the distal end of said applicator handle causing said applicator to pivot on said applicator support depression acting as a fulcrum to lever upwards the applicator handle and the applicator brush permitting said applicator to be easily grasped by a user,
   whereby said cover seals the applicator and said material within the tray until ready for use.

2. A single dose material and applicator package for dispensing a material as in claim 1 further comprising:
   a front applicator channel formed in said finger depression; and
   a rear applicator channel formed in said applicator support depression,
   whereby said applicator is capable of being held by said front and rear applicator channels.

3. A single dose material and applicator package for dispensing a dental material comprising:
   a plastic tray;
   an applicator well having a longitudinal length with a first end and a second end and a bottom formed in said plastic tray, said applicator well having a first lateral dimension over a majority of the longitudinal length;
   a material well formed in said plastic tray adjacent the first end;
   a ramp formed in said material well;
   a finger depression formed in the bottom of said applicator well adjacent said material well and extending into said applicator well;
   a front applicator channel formed in said finger depression;
   an applicator support depression formed in the bottom of said applicator well adjacent the second end of said applicator well and extending into said applicator well;
   a rear applicator channel formed in said applicator support depression;
   a wider portion of said applicator well formed adjacent an end of said applicator well, said wider portion having a second lateral dimension greater than the first lateral dimension of the majority of the longitudinal length of said applicator well, whereby a finger of a user is capable of passing through said wider portion;
   an applicator having an applicator handle and an applicator brush placed within the applicator well and positioned on top of said finger depression and said applicator support depression and held in a central position by said front applicator channel and said rear applicator channel;
   a dental material placed within said material well;
   a flange formed in a top surface of said tray forming a plane; and
   a cover removably affixed to said flange,
   whereby said cover seals the applicator and the material within the tray and upon removing said cover said applicator is capable of being pivoted on said applicator support depression upward by a user by placing a finger through said wider portion of said applicator well and pushing downward on a distal end of the applicator handle forcing the applicator brush away from said applicator well.

* * * * *